(12) United States Patent
Nishimura

(10) Patent No.: US 10,842,360 B2
(45) Date of Patent: Nov. 24, 2020

(54) OBJECTIVE OPTICAL SYSTEM

(71) Applicant: OLYMPUS CORPORATION, Hachioji (JP)

(72) Inventor: Sayaka Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 167 days.

(21) Appl. No.: 16/125,497

(22) Filed: Sep. 7, 2018

(65) Prior Publication Data

US 2019/0014976 A1 Jan. 17, 2019

Related U.S. Application Data

(63) Continuation of application No. PCT/JP2017/011698, filed on Mar. 23, 2017.

(30) Foreign Application Priority Data

Apr. 13, 2016 (JP) .................................. 2016-080314

(51) Int. Cl.
*A61B 1/00* (2006.01)
*G02B 13/04* (2006.01)
(Continued)

(52) U.S. Cl.
CPC ...... *A61B 1/00193* (2013.01); *A61B 1/00096* (2013.01); *A61B 1/00186* (2013.01);
(Continued)

(58) Field of Classification Search
CPC ............ A61B 1/00188; G02B 13/0045; G02B 13/04; G02B 13/18; G02B 23/2415; G02B 23/243; G02B 15/177
See application file for complete search history.

(56) References Cited

U.S. PATENT DOCUMENTS

2008/0180809 A1 7/2008 Igarashi
2011/0299175 A1 12/2011 Adachi
(Continued)

FOREIGN PATENT DOCUMENTS

JP 2004021158 A 1/2004
JP 2008107391 A 5/2008
(Continued)

OTHER PUBLICATIONS

International Preliminary Report on Patentability (IPRP) and Written Opinion dated Oct. 16, 2018 issued in International Application No. PCT/JP2017/011698.
(Continued)

*Primary Examiner* — Cara E Rakowski
(74) *Attorney, Agent, or Firm* — Holtz, Holtz & Volek PC

(57) ABSTRACT

An objective optical system consists of, in order from an object side, a front group, an intermediate group, and a rear group, wherein focusing is carried out from a far-point observation state to a near-point observation state by varying a focal length by moving the intermediate group along an optical axis, and the front group includes a first negative lens, and the first negative lens has a meniscus shape having an aspheric surface, and in any of the far-point observation state and the near-point observation state, the objective optical system satisfies the following conditional expressions (1) and (2)

$$|(1/2) \times \beta_f \times \beta t \times ((1/\beta_f)-1)| \leq 0.055 \qquad (1)$$

$$0.12 \leq Sa/FL \leq 0.44 \qquad (2).$$

8 Claims, 7 Drawing Sheets

(51) Int. Cl.
*G02B 13/18* (2006.01)
*G02B 23/26* (2006.01)
*G02B 13/00* (2006.01)
*G02B 15/177* (2006.01)

(52) U.S. Cl.
CPC ...... *A61B 1/00188* (2013.01); *A61B 1/00197* (2013.01); *G02B 13/0045* (2013.01); *G02B 13/04* (2013.01); *G02B 13/18* (2013.01); *G02B 15/177* (2013.01); *G02B 23/26* (2013.01)

(56) References Cited

U.S. PATENT DOCUMENTS

| | | |
|---|---|---|
| 2012/0057251 A1 | 3/2012 | Takato |
| 2012/0140095 A1* | 6/2012 | Bito .................. G02B 15/177 348/240.3 |
| 2012/0176529 A1* | 7/2012 | Matsuo ............... G02B 15/177 348/345 |
| 2014/0218811 A1 | 8/2014 | Yamamoto |
| 2015/0042773 A1 | 2/2015 | Uzawa et al. |
| 2016/0070094 A1 | 3/2016 | Togino |

FOREIGN PATENT DOCUMENTS

| | | |
|---|---|---|
| JP | 2011064933 A | 3/2011 |
| JP | 2011257465 A | 12/2011 |
| WO | 2011070930 A1 | 6/2011 |
| WO | 2013069265 A1 | 5/2013 |
| WO | 2014129089 A1 | 8/2014 |
| WO | 2014147856 A1 | 9/2014 |

OTHER PUBLICATIONS

International Search Report (ISR) dated Jun. 20, 2017 issued in International Application No. PCT/JP2017/011698.
Written Opinion dated Jun. 20, 2017 issued in International Application No. PCT/JP2017/011698.
Japanese Office Action dated Jan. 31, 2018 issued in counterpart Japanese Patent Application No. JP 2017-554922.
Chinese Office Action (and English translation thereof) dated Mar. 26, 2020, issued in counterpart Chinese Application No. 201780016158.X.

* cited by examiner

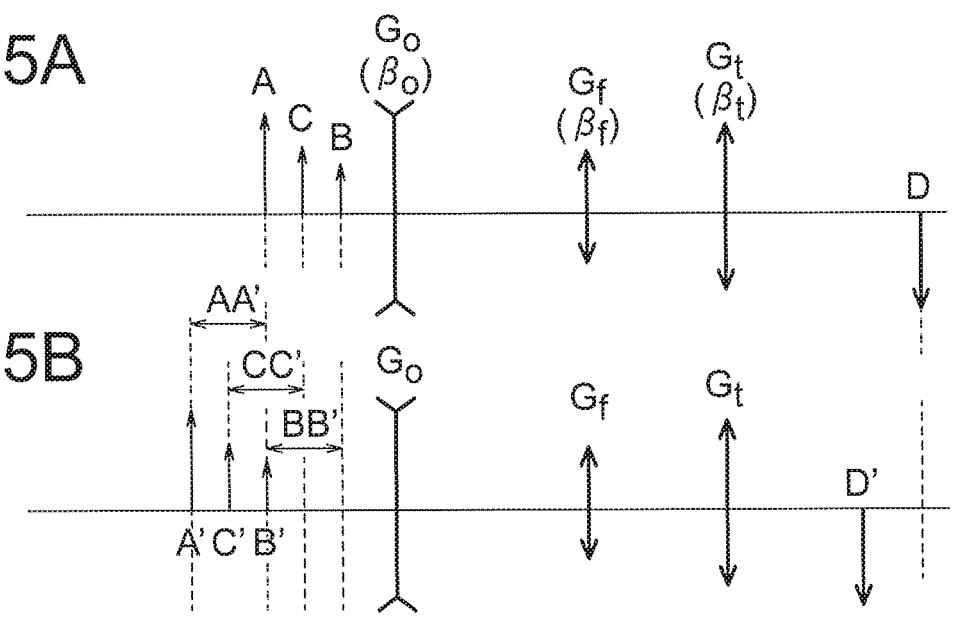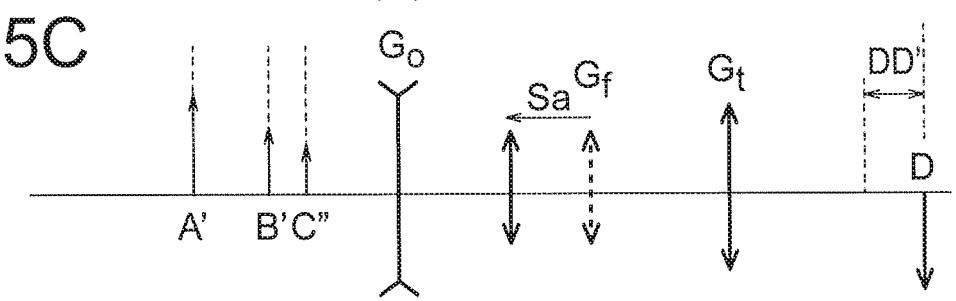
FIG. 5A
FIG. 5B
FIG. 5C

OBJECTIVE OPTICAL SYSTEM

CROSS-REFERENCE TO RELATED APPLICATION

The present application is a continuation application of PCT/JP2017/011698 filed on Mar. 23, 2017 which is based upon and claims the benefit of priority from Japanese Patent Application No. 2016-080314 filed on Apr. 13, 2016; the entire contents of which are incorporated herein by reference.

BACKGROUND OF THE INVENTION

Field of the Invention

The present invention relates to an objective optical system for an endoscope for stereoscopic observation, which enables magnified observation and has a focusing function.

Description of the Related Art

In recent years, in a medical field, for carrying out a precise and prompt surgery of a lesion, a surgical endoscope which enables stereoscopic observation is available. The existent stereoscopic endoscopes, because of having problems from an image quality point, are sought to have a high image quality.

Accordingly, a surgical endoscope which enables stereoscopic observation with a high image quality while maintaining an outer diameter of the endoscope, a depth of field, and contrast specifications as before, has been sought.

For achieving the high image quality while maintaining the outer diameter of endoscope, it is necessary to make a pixel pitch of an image sensor small. It has been known that when the pixel pitch of the image sensor is made small, the depth of field becomes narrow. For maintaining the depth of field, there is a method of making an F-number large. Here, as the F-number is made large, the contrast is degraded, and therefore it is not preferable.

In an objective optical system, by providing a focusing function, it is possible to focus to different object points. Therefore, it is desirable to provide the focusing function to an objective optical system. Objective optical systems provided with the focusing function have been disclosed in Japanese Patent Application Laid-open Publication No. 2011-257465, International Unexamined Patent Application Publication No. 2011/070930, Japanese Patent Application Laid-open Publication No. 2004-021158 and Japanese Patent Application Laid-open Publication No. 2011-064933.

SUMMARY OF THE INVENTION

An objective optical system according to at least some embodiments of the present invention consists of, in order from an object side:
a front group;
an intermediate group; and
a rear group, wherein
focusing is carried out from a far-point observation state to a near-point observation state by varying a focal length by moving the intermediate group along an optical axis, and
the front group includes a first negative lens, and the first negative lens has a meniscus shape having an aspheric surface, and in any of the far-point observation state and the near-point observation state, the objective optical system satisfies the following conditional expressions (1) and (2)

$$|(1/2) \times \beta f \times \beta t \times ((1/\beta f) - 1)| \leq 0.055 \quad (1)$$

$$0.12 \leq Sa/FL \leq 0.44 \quad (2)$$

where,
βf denotes a lateral magnification of the intermediate group,
βt denotes a lateral magnification of the rear group,
Sa denotes an amount of movement of the intermediate group at the time of focusing from the far-point observation state to the near-point observation state, and
FL denotes a focal length of the objective optical system, and
conditional expressions (1) and (2) are conditional expressions for the far-point observation state (object distance 60 mm) and the near-point observation state (object distance 31 mm).

An objective optical system according to at least some embodiments of the present invention consists of, in order from an object side:
a front group;
an intermediate group; and
a rear group, wherein
focusing is carried out from a far-point observation state to a near-point observation state by varying a focal length by moving the intermediate group along an optical axis, and
the intermediate group includes an aperture stop and a planoconvex lens of which an object side is a flat surface, and
in any of the far-point observation state and the near-point observation state, the objective optical system satisfies the following conditional expressions (1) and (2)

$$|(1/2) \times \beta f \times \beta t \times ((1/\beta f) - 1)| \leq 0.055 \quad (1)$$

$$0.12 \leq Sa/FL \leq 0.44 \quad (2)$$

where,
βf denotes a lateral magnification of the intermediate group,
βt denotes a lateral magnification of the rear group,
Sa denotes an amount of movement of the intermediate group at the time of focusing from the far-point observation state to the near-point observation state, and
FL denotes a focal length of the objective optical system, and
conditional expressions (1) and (2) are conditional expressions for the far-point observation state (object distance 60 mm) and the near-point observation state (object distance 31 mm).

BRIEF DESCRIPTION OF THE DRAWING

FIG. 5A, FIG. 5B, and FIG. 5C are other diagrams showing a relationship between the movement of the intermediate group along the optical axis and the image forming position;

DETAILED DESCRIPTION OF THE INVENTION

An objective optical system according to embodiments will be described below in detail by referring to the accompanying diagrams. However, the present invention is not restricted to the embodiments described below.

Figure 1A:
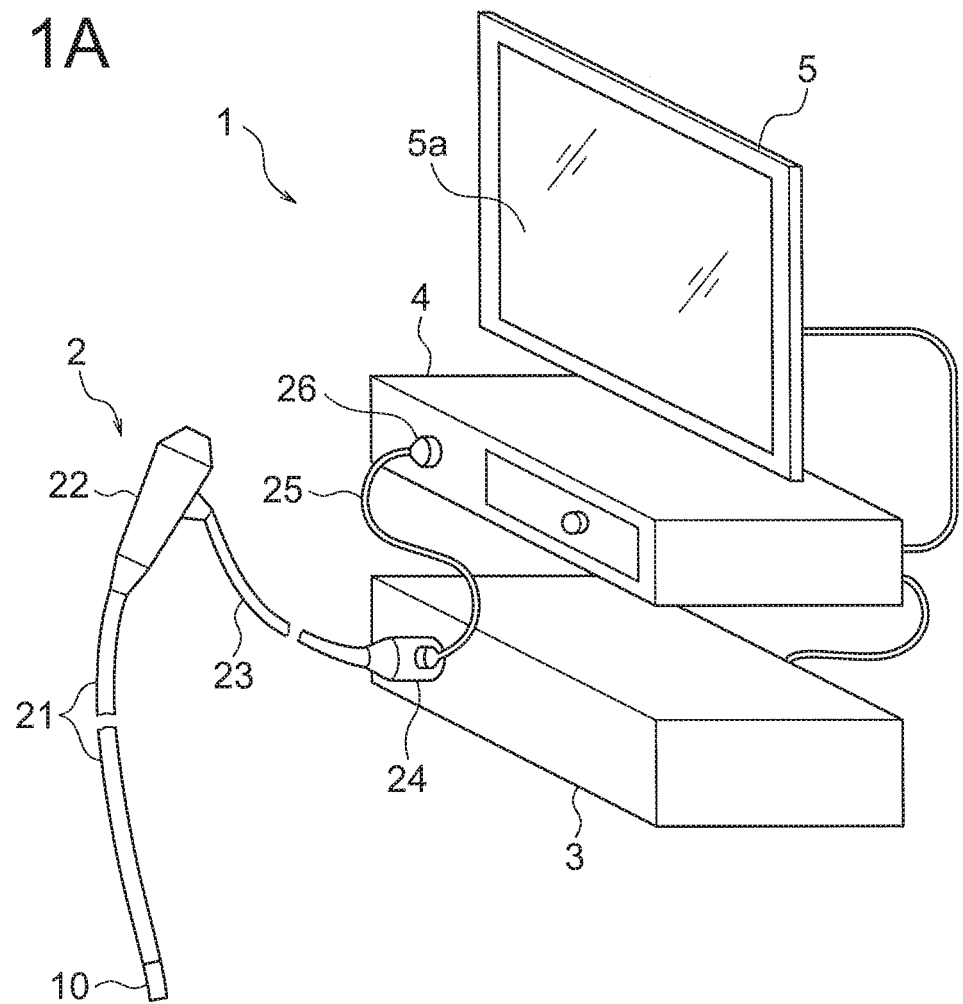
FIG. 1A is a diagram showing a schematic arrangement of an endoscope apparatus having an objective optical system according to an embodiment.

FIG. 1A is a diagram showing a schematic arrangement of an endoscope apparatus 1 having the objective optical system according to the embodiment. The endoscope apparatus 1 includes an electronic endoscope 2 in which an image sensor IMG is built-in as an image pickup unit, a light-source unit 3 having a light source which supplies illumination light to the electronic endoscope 2, an image processing unit 4 which carries out signal processing with respect to the image sensor IMG of the electronic endoscope 2, and a monitor 5 which displays an endoscope image by a video signal that is output via the image processing unit 4. A right-eye image and a left-eye image are displayed on a monitor screen 5a of the monitor 5.

The electronic endoscope 2 includes a long and slender insertion portion 21 having flexibility, in which the image sensor IMG is built-in, an operating portion 22 having a large width formed at a rear end of the insertion portion 21, a rigid tip portion 10, and a universal cord 23 extended from a rear portion of the operating portion 22. A connector 24 which is detachably connectible to the light-source unit 3 is provided to an end portion of the universal cord 23. An electric connector 26 which is detachably connectible to the image processing unit 4 is provided to an end portion of a connecting cord 25 extended from a side portion of the connector 24.

Next, an objective optical system according to the embodiments in the endoscope apparatus 1 will be described below.

First Embodiment

An objective optical system according to the first embodiment consists of, in order from an object side, a front group, an intermediate group, and a rear group, wherein a focal length varies by moving the intermediate group along an optical axis, and in any of a far-point observation state and a near-point observation state, the objective optical system satisfies the following conditional expressions (1) and (2).

$$|(1/2) \times \beta f \times \beta t \times ((1/\beta f)-1)| \leq 0.055 \quad (1)$$

$$0.12 \leq Sa/FL \leq 0.44 \quad (2)$$

where, $\beta f$ denotes a lateral magnification of the intermediate group, $\beta t$ denotes a lateral magnification of the rear group, Sa denotes an amount of movement of the intermediate group, and FL denotes a focal length of the objective optical system, and conditional expressions (1) and (2) are conditional expressions for the far-point observation state (object distance 60 mm) and the near-point observation state (object distance 31 mm).

In other words, parameters of conditional expressions (1) and (2) in the far-point observation state are, $\beta f$, which is the lateral magnification in the far-point observation state of the intermediate group, $\beta t$, which is the lateral magnification in the far-point observation state of the rear group, Sa, which is the amount of movement of the intermediate group, and FL, which is the focal length in the far-point observation state of the objective optical system.

Parameters of conditional expressions (1) and (2) in the near-point observation state are, $\beta f$, which is the lateral magnification in the near-point observation state of the intermediate group, $\beta t$, which is the lateral magnification in the near-point observation state of the rear group, Sa, which is the amount of movement of the intermediate group, and FL, which is the focal length in the far-point observation state of the objective optical system.

Figure 1B:
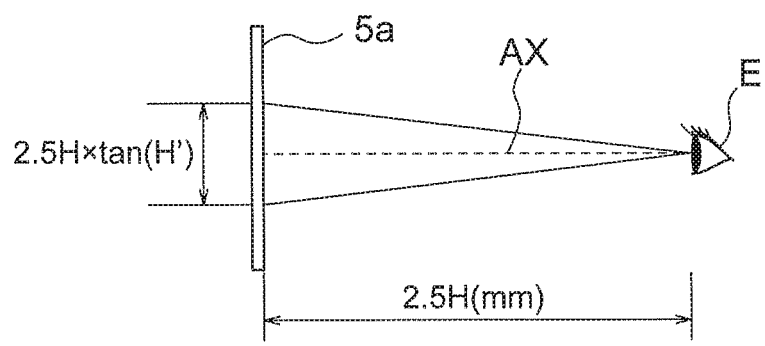
FIG. 1B is a diagram showing conditions for carrying out stereoscopic observation safely.

Conditional expression (1) will be described below. FIG. 1B shows a relationship between an observer's eye E and the monitor screen 5a based on the abovementioned ISO standards. In a stereoscopic vision, the larger the shift of corresponding points in the vertical direction, the more difficult is the fusion of images for the user. Moreover, when there is a vertical shift above a certain level, not only it is impossible to fuse the images but also it causes fatigue of the observer's eye E.

Furthermore, when a size in a vertical direction of the monitor 5a having a rectangular shape is let to be H, a comfortable visual distance, or in other words, a distance between the observer's eye E and the monitor screen 5a for stereoscopic vision is 4H in general. Here, sometimes, a medical doctor looks at the monitor 5a upon coming somewhat close at the time of surgery, and sometimes an operation room is small. Therefore, taking in to consideration the stereoscopic vision in surgery, even for the visual distance of 2.5 H, it is necessary to satisfy the abovementioned ISO standards.

Therefore, when an angle 15' of the abovementioned shift in vertical direction is converted to a value of vertical-center shift on the monitor screen 5a for stereoscopic vision, it becomes 2.5 H×tan (15') (mm).

Focusing by an actuator is carried out, and an amount of shift in a lens position due to shaking of lens frames is let to be a (mm). Even in a case in which the amount of shift a occurs due to shaking, for achieving comfortable and safe stereoscopic vision, with regard to an objective optical system, it is desired to make an amount of shift in the vertical direction of corresponding points of a left-eye image and a right-eye image on the monitor screen 5a not more than 2.5 H×tan (15').

This almost signifies that the amount of shift in the vertical direction with respect to a design state of one-eye's image is to be made not more than (1/2)×2.5 H×tan (15').

A proportion of the amount of shift in the vertical direction with respect to a size of the monitor screen 5a is (½)×2.5 H×tan (15')/H
=1.25×tan (15')
=0.0055.

In other words, focusing by actuator is carried out, and when a shift in the lens position occurs due to shaking of the lens frames, an acceptable amount of shift in the vertical direction from a center of an image sensor of an optical axis for each of an optical system of the left eye and an optical system for the right eye becomes 0.55%.

Moreover, the objective optical system of the present embodiment includes a front group Go, an intermediate group Gf, and a rear group Gt. A lateral magnification of the front group Go is let to be βo, a lateral magnification of the intermediate group Gf is let to be βf, and a lateral magnification of the rear group Gt is let to be βt. The lateral magnification is a value when an object distance is 60 mm for a far-point object and when an object distance is 31 mm for a near-point object.

Figure 2A:
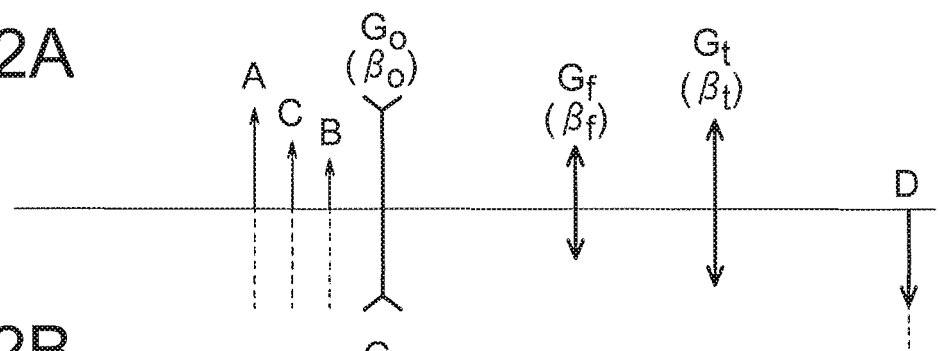
FIG. 2A, FIG. 2B, and FIG. 2C are diagrams showing a relationship between a movement of an intermediate group along an optical axis and an image forming position.
Figure 2B:
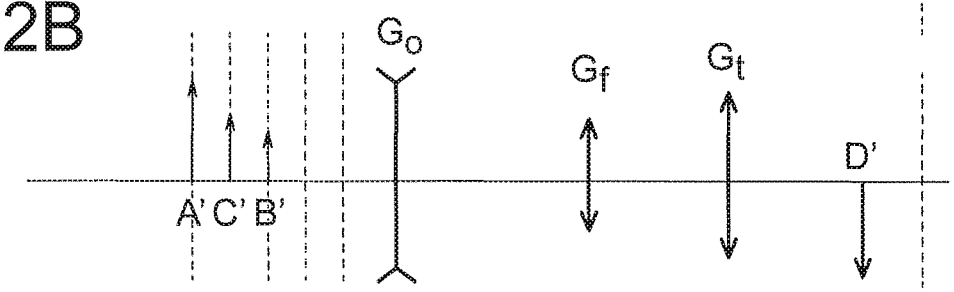
Figure 2C:
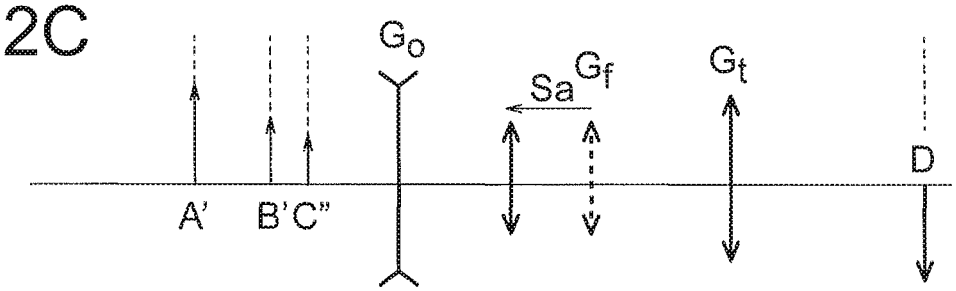

FIG. 2A, FIG. 2B, and FIG. 2C are diagrams showing a relationship between a movement of the intermediate group Gf along the optical axis and an image forming position.

FIG. 2A shows an object image relationship in the near-point observation state. The description will be made with reference to a lens position in the near-point observation state. An object A is formed as an image as an object B by the front group Go. Moreover, an object B is formed as an image as an object C by the intermediate group Gf. Furthermore, an object C is formed as an image D by the rear group Gt.

Next, when the far-point observation is carried out with the lens arrangement shown in FIG. 2A, an object A' is formed as an image as an object B' by the front group Go. Moreover, an object B' is formed as an image as an object C' by the intermediate group Gf. Furthermore, an object C' is formed as an image D' by the rear group Gt.

Consequently, as shown in FIG. 2C, the intermediate group Gf moves toward the object side with respect to the object A' by only the distance Sa (mm). Accordingly, even in the far-point observation state, it is possible to form the object A' as the image D on an image sensor surface.

Figure 3A:
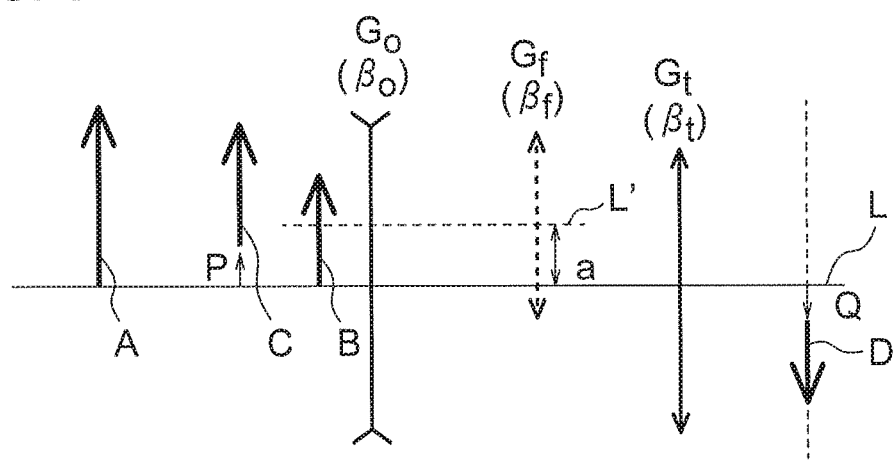
FIG. 3A is a diagram showing a relationship between a shift of the intermediate group in a direction perpendicular to the optical axis and an image.
Figure 3B:
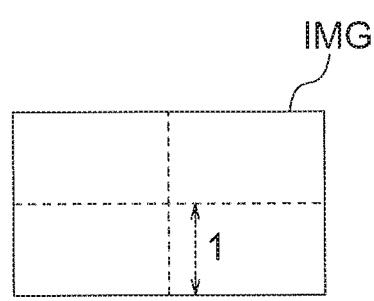
FIG. 3B is a diagram showing a region in an image sensor.

Next, a case in which the intermediate group Gf undergoes a position shift in a plane perpendicular to an optical axis L will be taken into consideration. FIG. 3A is a diagram showing a relationship between an image and a shift of the intermediate group Gf in a direction perpendicular to the optical axis L. FIG. 3B is a diagram showing a region on the image sensor IMG. As shown in FIG. 3A, a case in which an optical axis L' of the intermediate group Gf shifts in an upward direction of a paper surface only by an amount of shift a with respect to the optical axis L, is taken into consideration.

The object A is formed as an image as the object B by the front group Go. When the object B passes through the intermediate group of the lateral magnification βf, the optical axis L' of the intermediate group Gf shifts only by an amount a. Consequently, the object C formed by the intermediate group Gf is shifted from the optical axis L of the front group Go. An amount of shift P of the object C from the optical axis L at this time is indicates by the following expression.

$$P = a - a \times \beta f = a(1 - \beta f)$$

The object C is formed as an image on an image sensor surface by the rear group Gt. At this time, as shown in FIG. 3A, the image D becomes an image shifted from the optical axis L only by an amount Q. This amount of shift Q becomes an amount of center shift, and is indicated by the following expression.

$$Q = a \times (1 - \beta f) \times \beta t$$

Next, the amount of shift Q is converted to a size on an object plane.

This becomes, $$Q/(\beta o \times \beta f \times \beta t) = a/\beta o \times ((1/\beta f) - 1).$$

(Here, βt is a lateral magnification of the rear group Gt.) This is the amount of center shift on the object plane.

On the other hand, as shown in FIG. 3B, let a size of half of a vertical opposite side of the image sensor IMG be 1. A visual field range in the vertical direction on the object plane is indicated by the following expression.

$$(1/(\beta o \times \beta f \times \beta t)) \times 2 = 2/(\beta o \times \beta f \times \beta t)$$

Consequently, a proportion with respect to the overall visual field of the amount of center shift of the object plane is $$(a/\beta o \times ((1/\beta f) - 1))/((2/(\beta o \times \beta f \times \beta t)) = (\frac{1}{2})\beta f \times \beta t \times a((1/\beta f) - 1).$$

Moreover, it is desirable that an acceptable amount for safety of the stereoscopic vision is not more than 0.0055 as mentioned above, and that the following conditional expression (A) is satisfied, taking into account that the direction of shift is each of the upward direction and the downward direction.

$$|(\frac{1}{2})\beta f \times \beta t \times a((1/\beta f) - 1)| \leq 0.0055 \quad (A)$$

Here, the amount of shift in a misalignment of lens is determined by an accuracy of components and an accuracy of assembling. Even when highly accurate components and highly accurate assembling process is used, the amount of shift a in the misalignment of the intermediate group Gf becomes 0.1 mm or more.

Therefore, when a ≥0.1 is substituted in conditional expression (A), the following conditional expression (1) is achieved.

$$|(\frac{1}{2})\beta f \times \beta t \times ((1/\beta f) - 1)| \leq 0.055 \quad (1)$$

Next, the amount of movement of the intermediate group Gf will be taken into consideration. Let the amount of movement of the intermediate group Gf along the optical axis L be Sa, and a focal length of the objective optical system be FL. When Sa/FL<0.12, or in other words, when the amount of movement Sa is small, an effect of an accuracy of a stopping position of the intermediate group Gf in a direction of the optical axis L becomes large. Consequently, due to a small shift in position of the intermediate group Gf, the best object position in a paraxial region changes largely.

On the other hand, when Sa/FL>0.44, or in other words, when the amount of movement Sa is large, since a lens diameter of the intermediate group Gf becomes large, it is not suitable for an objective optical system of a stereoscopic endoscope.

In the present embodiment, taking into consideration the points mentioned above, it is desirable to satisfy the following conditional expression (2).

$$0.12 \leq Sa/FL \leq 0.44 \quad (2)$$

Moreover, according to a preferable aspect of the present invention, it is desirable that the objective optical system is an objective optical system to be used in a stereoscopic endoscope.

Accordingly, it is possible to suppress an amount of shift in the vertical direction of the left-eye image and the right-eye image at the time of stereoscopic observation, and to carry out comfortable and safe stereoscopic observation.

Moreover, according to a preferable aspect of the present invention, it is desirable to satisfy the following conditional expression (3).

$$|(1/2) \times \beta f \times \beta t \times ((1/\beta f) - 1)| \leq 0.044 \quad (3)$$

The lateral magnification is a value when the object distance is 60 mm for a far-point object and when the object distance is 31 mm for a near-point object.

In a medical field where endoscope is used, without restricting to the abovementioned visual distance 2.5 H, it is possible to observe the monitor screen 5a at the visual distance 2H depending on an area of the operating room and standing positions of people other than doctor.

With that, the following expression is established.

$$(1/2) \times \beta f \times \beta t \times a((1/\beta f) - 1) \leq 2H \times \tan(15') \times (1/2)/H =$$

$$\tan(15') = 0.0044$$

Similarly as in the abovementioned case, it is desirable to satisfy the following conditional expression (3) by substituting a=0.1.

$$|(1/2) \times \beta f \times \beta t \times ((1/\beta f) - 1)| \leq 0.044 \quad (3)$$

Next, an arrangement of the objective optical system will be described below. The objective optical system according to the embodiment includes in order from the object side, the front group Go having a negative refractive power, the intermediate group Gf having a positive refractive power, and the rear group Gt having a positive refractive power.

The front group Go includes a first meniscus negative (concave) lens and a cemented lens having a negative refractive power in which, a negative lens and a positive lens are cemented.

The intermediate group Gf includes an aperture stop S and a planoconvex positive lens of which an object side is a flat surface.

The rear group Gt includes in order from the object side, a cemented lens having a positive refractive power in which a negative lens and a positive lens are cemented, a cemented lens having a positive refractive power in which a negative lens and a positive lens are cemented, and a cemented lens having a positive refractive power in which a positive lens and a negative lens are cemented.

It is desirable that the first negative (concave) lens has an aspheric shape. For carrying out the stereoscopic observation comfortably, it is desirable to make small a distortion of each of the left-eye image and the right-eye image. For this, by using the aspheric shape for the first negative (concave) lens, it is possible to make the distortion small while realizing small-sizing of a lens diameter.

Moreover, in a case of disposing the aperture stop S in the front group Go, lenses in the rear group Gt become large. In a case of disposing the aperture stop S in the rear group Gt, not only a lens diameter of the front group Go becomes large but also a lens diameter of the intermediate group Gf becomes large. In the intermediate group Gf, since it is necessary to secure a space for an actuator for focusing between a diameter of the overall optical system and a diameter of the intermediate group Gf, it is desirable to make the lens diameter of the intermediate group Gf small. For this, it is desirable to dispose the aperture stop S in the intermediate group Gf, and to suppress the lens diameter of the intermediate group Gf.

Furthermore, a shape of the positive lens immediately next to an image side of the aperture stop S in the intermediate group Gf will be described below. In a case in which an object-side surface of the positive lens has a curvature, a flat surface of the aperture stop S and a convex surface or a concave surface of the positive lens interfere, thereby degrading assemblability. Therefore, it is desirable that the object-side surface of the positive lens is a flat surface.

Moreover, at the time of driving the intermediate group by an actuator, it is necessary to make the actuator large in accordance with the weight of the lens that is to be driven. Consequently, for small-sizing of the optical system, it is advantageous that the lens to be driven is light-weight. For this, it is desirable that in the intermediate group Gf, there is one lens having a power.

Furthermore, for achieving a high image quality while realizing small-sizing of the objective optical system, it is desirable to reduce a chromatic aberration by using three sets of cemented lenses in the rear group Gt in order to cope with a small image sensor with a small pixel pitch.

Examples will be described below.

Example 1

Figure 4A:
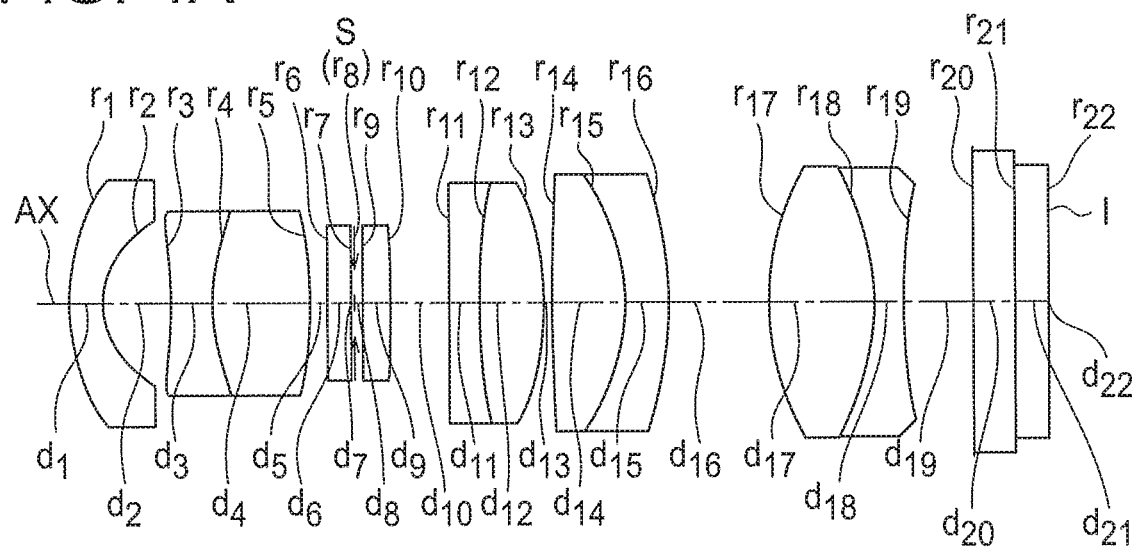
FIG. 4A is a lens cross-sectional view in a far-point observation state of an objective optical system according to an example 1.
Figure 4B:
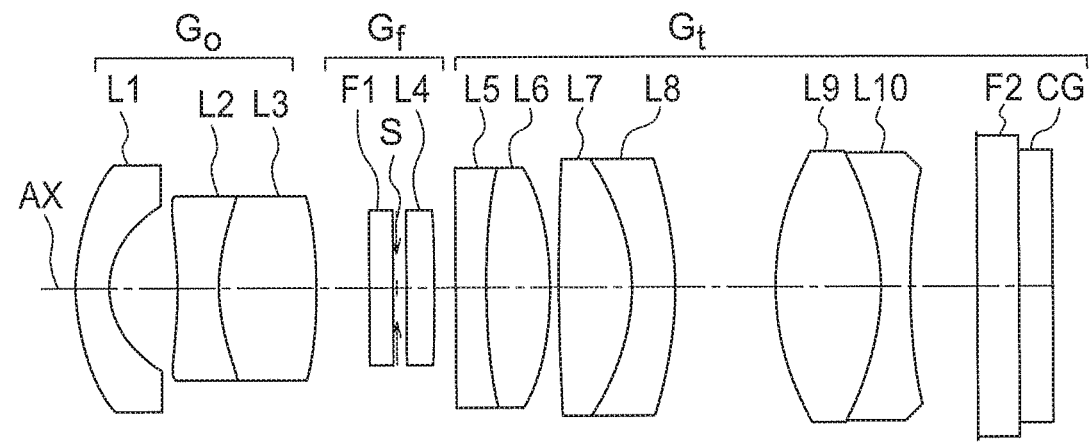
FIG. 4B is a lens cross-sectional view in a near-point observation state of the objective optical system according to the example 1.

An objective optical system according to an example 1 will be described below. FIG. 4A is a lens cross-sectional view in a far-point observation state of the objective optical system according to the present example. FIG. 4B is a lens cross-sectional view in a near-point observation state of the objective optical system according to the present example.

The objective optical system of the present example includes in order from an object side, a front group Go having a negative refractive power, an intermediate group Gf having a positive refractive power, and a rear group Gt having a positive refractive power.

The front group Go includes a negative meniscus lens L1 having a convex surface directed toward the object side, a biconcave negative lens L2, and a biconvex positive lens L3. The negative lens L2 and the positive lens L3 are cemented.

The intermediate group Gf includes a filter F1, an aperture stop S, and a planoconvex positive lens L4 having a flat surface directed toward the object side.

The rear group Gt includes a planoconcave negative lens L5 having a flat surface directed toward the object side, a biconvex positive lens L6, a biconvex positive lens L7, a negative meniscus lens L8 having a convex surface directed toward an image side, a biconvex positive lens L9, a biconcave negative lens L10, a cover glass F2, and a CCD (charge coupled device) cover glass CG. The negative lens L5 and the positive lens L6 are cemented. The positive lens L7 and the negative meniscus lens L8 are cemented. The positive lens L9 and the negative lens L10 are cemented.

Moreover, the cover glass F2 and the CCD cover glass CG are cemented. Furthermore, a YAG (yttrium aluminum garnet) laser cut coating is applied to an object side of the filter F1 which is an infra-red absorbing filter and an LD laser cut coating is applied to an image side of the filter F1. At the time of focusing from the far-point observation state (FIG. 4A) to the near-point observation state (FIG. 4B), the intermediate group Gf moves toward the image (image plane I) side.

Example 2

In an objective optical system according to an example 2, by a value of the abovementioned conditional expression (2)

being near a lower limit value, or in other words, by making an amount of lens drive of the intermediate group Gf small, the lens diameter has become small. However, on the other hand, the smaller the amount of lens drive of the intermediate group Gf, in the paraxial region, a difference in the best object position of a right-eye optical system and the best object position of a left-eye optical system becomes larger.

For instance, near a working distance of 60 mm to 100 mm at the time of stereoscopic observation, when the difference in the best object position for the left-eye optical system and the right-eye optical system becomes 10 mm or more than 10 mm, the best object position as a stereoscopic image is not fixed, and a medical treatment by a minute stereoscopic vision cannot be carried out correctly.

When a position accuracy of a lens to be driven is ±30 μm, in the present example, the difference in the object position (object distance) in the paraxial region for the left-eye optical system and the right-eye optical system is 8.4 mm, which is within an acceptable range.

Here, the difference in the best object position in the paraxial region for the right-eye optical system and the left-eye optical system is derived as described below. When a distance (d5) from a fifth surface is plus 30 μm than design value, or in other words, when a distance (d10) from a tenth surface is minus 30 μm than design value, the best image-plane position in the paraxial region is shifted by 0.00232 mm to an opposite side of the object side, as compared to an initial state (the design value state).

Similarly, when the distance (d5) from the fifth surface is minus 30 μm than design value, or in other words, when the distance (d10) from the tenth surface is plus 30 μm than design value, the best image-plane position in the paraxial region is shifted by 0.00233 mm to the opposite side of the object side, as compared to the initial state (the design value state).

It is possible to convert to a distance at the object surface by dividing the shift widths by a square of magnifying power. When converted to the distance on the object surface, it becomes 8.4 mm.

When a value of conditional expression (2) falls below a lower limit value, and Sa/FL<0.12, an amount of movement of a lens becomes small. Consequently, depending on a positional accuracy in an optical axial direction of a lens to be driven, the difference in the best object position in the paraxial region for the left-eye optical system and the right-eye optical system becomes excessively large. Therefore, it is desirable to satisfy a relationship 0.12≤Sa/FL.

Moreover, the difference in the object position (object distance) 60 mm in the paraxial region for the left-eye optical system and the right-eye optical system being suppressed to be less than 10 mm has the same significance as that of satisfying the following conditional expression (4).

$|(\beta o \times \beta f)^2/(1-\beta f^2)|>0.006$ (4)

A method for deriving conditional expression (4) will be described below. A fact that a shift of the optical system for one eye with respect to a design value of the best object position is less than 5 mm when a positional accuracy of the lens to be driven is shifted by 30 μm is same as a condition of moving the intermediate group Gf by 30 μm such that the image plane does not move, when the object position is shifted by 5 mm.

Such concept will be described below by using FIG. 5A, FIG. 5B, and FIG. 5C. FIG. 5A shows a lens cross-sectional view at a position of the object A at a design value. FIG. 5B shows a lens cross-sectional view in a state of the object shifted by 5 mm. FIG. 5C is a diagram showing a lens cross-sectional view in a case of correction being carried out such that a position of an image plane does not change even when the object has shifted.

As shown in FIG. 5A, FIG. 5B, and FIG. 5C, a case in which the position of the object has shifted by 5 mm toward a far-point side as an object A' with a lens position at a design value as a reference, is shown below.

distance between $A$ and $A'$=5 (mm)

distance between $B$ and $B'$=5×$\beta o^2$ (mm)

distance between $C$ and $C'$=5×$\beta o^2 \times \beta f^2$ (mm)

distance between $D$ and $D'$=5×$\beta o^2 \times \beta f^2 \times \beta r^2$ (mm)

In such manner, when the object A shifts 5 mm toward the far-point side, as object A', there is a difference of D–D' between the final image position and an image forming position.

Therefore, in order that the difference D–D' of the image forming position becomes 0, moving the intermediate group Gf by Sa=30 μm is to be considered. Here, the rear group Gt is common in the near-point observation state and the far-point observation state. Therefore, the intermediate group Gf is to be moved such that C–C' becomes 0 (C–C'=0).

However, when the intermediate group Gf is moved by 30 μm, not that the object B' moves by 30 μm but an effect of a lateral magnification (=βf²) of the intermediate group Gf is subtracted.

The abovementioned point will be described below by using an expression.

distance between $C$ and $C'$-(30 μm-30 μm×$\beta f^2$)=0

When the distance between C and C' is substituted, then 5 mm×$\beta o^2 \times \beta f^2$-(30 μm-30 μm×$\beta f^2$)=0

Or in other words, $$(\beta o \times \beta f)^2 / (1 - \beta f^2) = 30 \text{ μm}/5 \text{ mm}$$
$$= 0.006$$

Moreover, by taking into consideration a reference numeral as the positional accuracy is ±30 μm, and furthermore, by taking into consideration a fact that a range in which the shift in the best object position that is acceptable with respect to the design value is less than 5 mm, the following conditional expression (4) is achieved.

$|(\beta o \times \beta f)^2/(1-\beta f^2)|>0.006$ (4)

The lateral magnification is a value when the object distance is 60 mm for a far-point object and when the object distance is 31 mm for a near-point object.

Figure 6A:
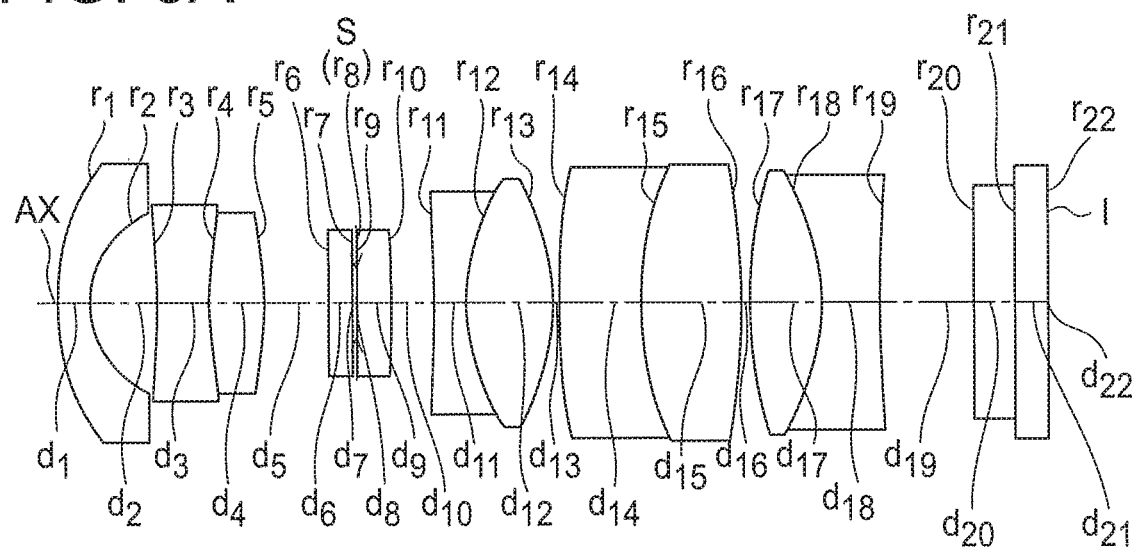
FIG. 6A is a lens cross-sectional view of a far-point observation state of an objective optical system according to an example 2.
Figure 6B:
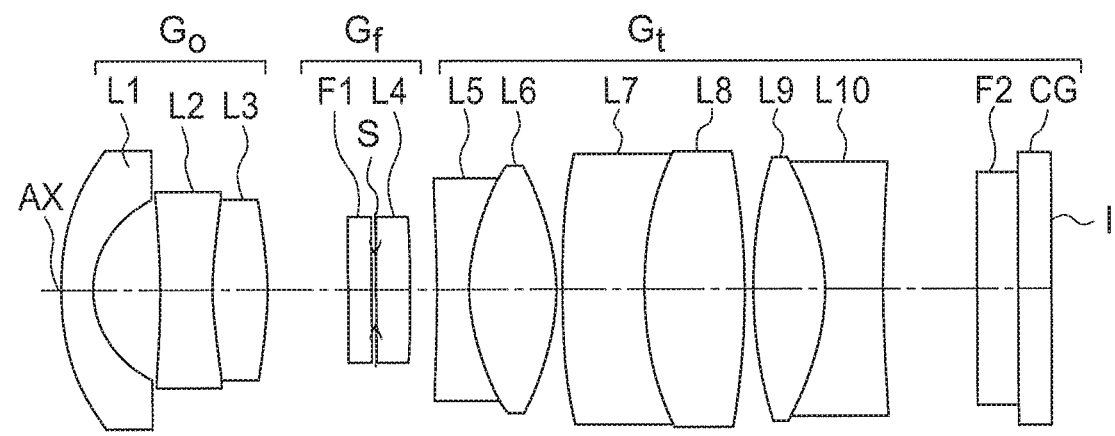
FIG. 6B is a lens cross-sectional view of a near-point observation state of the objective optical system according to the example 2.

The objective optical system according to the example 2 will be described below. FIG. 6A is a lens cross-sectional view in a far-point observation state of the objective optical system according to the present example. FIG. 6B is a lens cross-sectional view in a near-point observation state of the objective optical system according to the present example.

The objective optical system of the present example includes in order from an object side, a front group Go having a negative refractive power, an intermediate group Gf having a positive refractive power, and a rear group Gt having a positive refractive power.

The front group Go includes a negative meniscus lens L1 having a convex surface directed toward the object side, a biconcave negative lens L2, and a biconvex positive lens L3. The negative lens L2 and the positive lens L3 are cemented.

The intermediate group Gf includes a filter F1, an aperture stop S, and a planoconvex positive lens L4 having a flat surface directed toward the object side.

The rear group Gt includes a biconcave negative lens L5, a biconvex positive lens L6, a negative meniscus lens L7 having a convex surface directed toward the object side, a biconvex positive lens L8, a biconvex positive lens L9, a biconcave negative lens L10, a cover glass F2, and a CCD cover glass CG. The negative lens L5 and the positive lens L6 are cemented. The negative meniscus lens L7 and the positive lens L8 are cemented. The positive lens L8 and the negative lens L10 are cemented.

Moreover, the cover glass F2 and the CCD cover glass CG are cemented. Furthermore, a YAG laser cut coating is applied to an object side of the filter F1 which is an infra-red absorbing filter and an LD laser cut coating is applied to an image side of the filter F1. At the time of focusing from the far-point observation state (FIG. 6A) to the near-point observation state (FIG. 6B), the intermediate group Gf moves toward the image (image plane I) side.

Example 3

In an objective optical system according to an example 3, with a concept similar to that of the example 2, when the positional accuracy of an intermediate group Gf is ±0.03 mm, the difference in the best image-plane position in a paraxial region for a left-eye optical system and a right-eye optical system is 1.15 mm, and the best object position as a stereoscopic image is clear. This is due to increasing a drive amount of the intermediate group Gf which is a lens to be driven, and making large a radius of curvature of an image-plane side of the lens to be driven.

On the other hand, since a light-ray height increases as the amount of driving of the intermediate group Gf is increased, a lens diameter becomes large. In a stereoscopic endoscope with 10 mm front-tip diameter of endoscope, two objective optical systems have been built-in.

Considering a thickness of a lens frame of each optical system, it is desirable that a lens diameter of one optical system is not more than 4 mm. In the objective optical system according to the present example, the maximum lens diameter being 3.9 mm, it is within an acceptable range.

Moreover, when a lens to be driven having a large radius of curvature such that $|(1/2) \times \beta f \times \beta t \times ((1/\beta f)-1)| < 0.004$ is used, it is necessary to increase the drive amount. In this case, since the lens diameter is more than 4 mm, it is not suitable for a stereoscopic endoscope. Therefore, it is desirable to satisfy the following conditional expression (5).

$$0.004 \leq (1/2) \times \beta f \times \beta t \times ((1/\beta f)-1) \quad (5)$$

The lateral magnification is a value when the object distance is 60 mm for a far-point object and when the object distance is 31 mm for a near-point object.

Figure 7A:
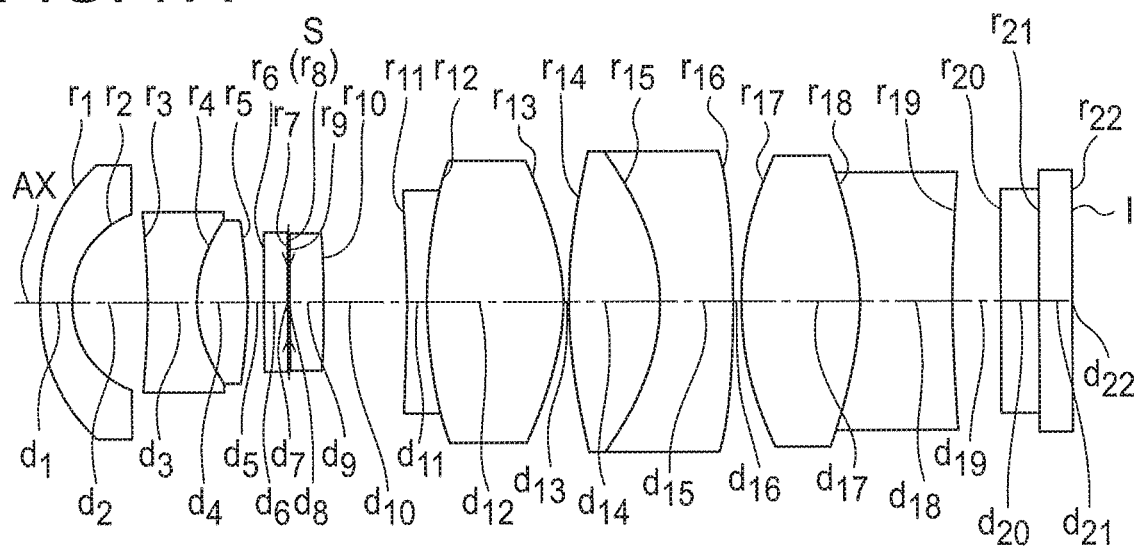
FIG. 7A is a lens cross-sectional view of a far-point observation state of an objective optical system according to an example 3.
Figure 7B:
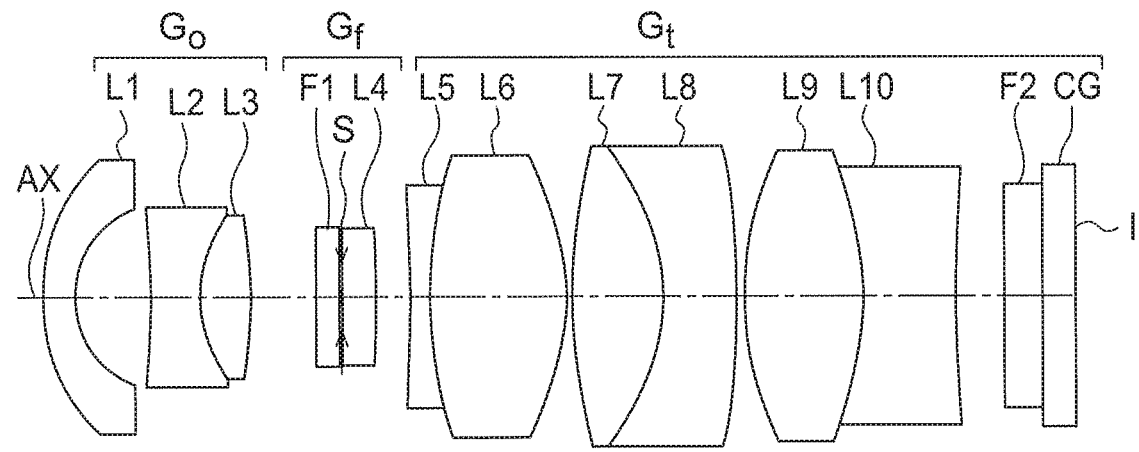
FIG. 7B is a lens cross-sectional view of a near-point observation state of the objective optical system according to the example 3.

The objective optical system according to the example 3 will be described below. FIG. 7A is a lens cross-sectional view in a far-point observation state of the objective optical system according to the present example. FIG. 7B is a lens cross-sectional view in a near-point observation state of the objective optical system according to the present example.

The objective optical system of the present example includes in order from an object side, a front group Go having a negative refractive power, an intermediate group Gf having a positive refractive power, and a rear group Gt having a positive refractive power.

The front group Go includes a negative meniscus lens L1 having a convex surface directed toward the object side, a biconcave negative lens L2, and a biconvex positive lens L3. The negative lens L2 and the positive lens L3 are cemented.

The intermediate group Gf includes a filter F1, an aperture stop S, and a planoconvex positive L4 having a flat surface directed toward the object side.

The rear group Gt includes a biconcave negative lens L5, a biconvex positive lens L6, a biconvex positive lens L7, a negative meniscus lens L8 having a convex surface directed toward an image side, a biconvex positive lens L9, a biconcave negative lens L10, a cover glass F2, and a CCD cover glass CG. The negative lens L5 and the positive lens L6 are cemented. The positive lens L7 and the negative meniscus lens L8 are cemented. The positive lens L9 and the negative lens L10 are cemented.

Moreover, the cover glass F2 and the CCD cover glass CG are cemented. Furthermore, a YAG laser cut coating is applied to an object side of the filter F1 which is an infra-red absorbing filter and an LD laser cut coating is applied to an image side of the filter F1. At the time of focusing from the far-point observation state (FIG. 7A) to the near-point observation state (FIG. 7B), the intermediate group Gf moves toward the image (image plane I) side.

Numerical data for each example is shown below. Regarding symbols, r denotes a radius of curvature of each lens surface, d denotes a distance between each lens surfaces, ne denotes a refractive index of each lens for an e-line, vd denotes Abbe number for each lens, and * denotes an aspheric surface.

Moreover, an aspheric surface shape is expressed by the following expression when a conical coefficient is let to be k and an aspheric surface coefficient is let to be A4, A6, A8, and A10, with z as an optical axial direction and y as a direction orthogonal to the optical axis.

$$Z=(y^2/r)/[1+\{1-(1+k)(y/r)^2\}^{1/2}]+A4y^4+A6y^6+A8y^8+A10y^{10}$$

Moreover, in the aspheric surface coefficient, 'e$^{-n}$,' (n is an integer) indicates '10$^{-n}$'. Symbols for these various basic values are same in numerical data of the examples.

Furthermore, f denotes a focal length of the overall system, fo denotes a focal length of the front group, ff denotes focal length of the intermediate group, and ft denotes a focal length of the rear group.

Example 1

| Unit mm | | | | |
|---|---|---|---|---|
| Surface data | | | | |
| Surface no. | r | d | ne | vd |
| 1* | 2.9142 | 0.4 | 1.81078 | 40.88 |
| 2* | 1.0606 | 0.84 | 1 | — |
| 3 | −18.377 | 0.5 | 2.01169 | 28.27 |
| 4 | 2.634 | 1.2 | 1.85504 | 23.78 |
| 5 | −8.532 | Variable | 1 | — |
| 6 | ∞ | 0.3 | 1.523 | 65.13 |
| 7 | ∞ | 0.03 | 1 | — |
| 8(Stop) | ∞ | 0.11 | 1 | — |
| 9 | ∞ | 0.35 | 1.65425 | 58.55 |
| 10 | −35.645 | Variable | 1 | — |
| 11 | ∞ | 0.4 | 2.01169 | 28.27 |
| 12 | 9.972 | 0.78 | 1.80642 | 34.97 |
| 13 | −3.375 | 0.08 | 1 | — |
| 14 | 24.688 | 0.9 | 1.73234 | 54.68 |

-continued

| Unit mm | | | | |
|---|---|---|---|---|
| 15 | −2.782 | 0.53 | 1.93429 | 18.9 |
| 16 | −5.625 | 1.2453 | 1 | — |
| 17 | 3.375 | 1.3 | 1.73234 | 54.68 |
| 18 | −3.375 | 0.35 | 2.01169 | 28.27 |
| 19 | 8.042 | 0.856 | 1 | — |
| 20 | ∞ | 0.5 | 1.51825 | 64.14 |
| 21 | ∞ | 0.4 | 1.507 | 63.26 |
| 22 | ∞ | 0 | 1 | — |
| Image pickup surface(Imageplane) | ∞ | | | |

Aspheric data

1st surface k = 8.03790546E−01
A4 = 7.54607261E−04, A6 = 5.60340795E−04, A8 = −1.85655955E−04

2nd surface k = −1.13771745E−01
A4 = 2.51411174E−03, A6 = −7.25176861E−04, A8 = 4.59260377E−03

Various data

| Surface no. | far-point object (object distance 60 mm) | near-point object (object distance 31 mm) |
|---|---|---|
| d5 | 0.21 | 0.68 |
| d10 | 0.72 | 0.25 |

| far-point object distance | 60 mm |
|---|---|
| near-point object distance | 31 mm |
| f | 1.4421(far-point object state) |
| f | 1.4226(near-point object state) |
| fo | −2.415 |
| ff | 54.482 |
| ft | 2.510 |

Example 2

| Unit mm | | | | |
|---|---|---|---|---|
| Surface data | | | | |
| Surface no. | r | d | ne | vd |
| 1* | 3.2321 | 0.4171 | 1.88815 | 40.76 |
| 2* | 1.2533 | 0.8296 | 1 | — |
| 3 | −9.4906 | 0.6585 | 1.88815 | 40.76 |
| 4 | 5.6876 | 0.6453 | 1.81264 | 25.42 |
| 5 | −7.4996 | Variable | 1 | — |
| 6 | ∞ | 0.3 | 1.523 | 65.13 |
| 7 | ∞ | 0.0381 | 1 | — |
| 8(Stop) | ∞ | 0 | 1 | — |
| 9 | ∞ | 0.4172 | 1.65425 | 58.55 |
| 10 | −24.891 | Variable | 1 | — |
| 11 | −15 | 0.4 | 1.85694 | 30.05 |
| 12 | 2.8146 | 1.0659 | 1.82017 | 46.62 |
| 13 | −3.1609 | 0.088 | 1 | — |
| 14 | 10.5207 | 1.0119 | 1.69401 | 54.82 |
| 15 | 4.2838 | 1.2275 | 1.85646 | 40.78 |
| 16 | −9.3472 | 0.1 | 1 | — |
| 17 | 5.6938 | 0.8964 | 1.6052 | 65.44 |
| 18 | −3.0462 | 0.7121 | 1.86784 | 22.73 |
| 19 | 17.1028 | 1.1554 | 1 | — |
| 20 | ∞ | 0.5 | 1.51825 | 64.14 |
| 21 | ∞ | 0.4 | 1.507 | 63.26 |
| 22 | ∞ | 0.0045 | 1 | — |
| Image pickup surface(Image plane) | ∞ | | | |

Aspheric data

1st surface k = −2.08993267E−03
A4 = 9.74800028E−03, A6 = 9.85707847E−04, A8 = −5.13568231E−05

2nd surface k = −3.35531252E−03
A4 = 7.48405269E−03, A6 = −1.06283300E−04, A8 = 4.94990559E−03

Various data

| Surface no. | far-point object (object distance 60 mm) | near-point object (object distance 31 mm) |
|---|---|---|
| d5 | 0.81862 | 1.00642 |
| d10 | 0.54828 | 0.36047 |

| far-point object distance | 60 mm |
|---|---|
| near-point object distance | 31 mm |
| f | 1.4507(far-point object state) |
| f | 1.4406(near-point object state) |
| fo | −2.843 |
| ff | 38.045 |
| ft | 2.581 |

Example 3

| Unit mm | | | | |
|---|---|---|---|---|
| Surface data | | | | |
| Surface no. | r | d | ne | vd |
| 1* | 2.9263 | 0.4 | 1.81078 | 40.88 |
| 2* | 1.2054 | 0.9796 | 1 | — |
| 3 | −7.3704 | 0.6415 | 1.83932 | 37.16 |
| 4 | 1.6853 | 0.6453 | 1.81264 | 25.42 |
| 5 | −6.9478 | Variable | 1 | — |
| 6 | ∞ | 0.3005 | 1.523 | 65.13 |
| 7 | ∞ | 0.035 | 1 | — |
| 8(Stop) | ∞ | 0 | 1 | — |
| 9 | ∞ | 0.4131 | 1.65425 | 58.55 |
| 10 | −164.0304 | Variable | 1 | — |
| 11 | −20.1282 | 0.2365 | 1.86784 | 22.73 |
| 12 | 5.5162 | 1.7651 | 1.82017 | 46.62 |
| 13 | −3.6175 | 0.088 | 1 | — |
| 14 | 7.2261 | 1.1525 | 1.77621 | 49.6 |
| 15 | −2.9888 | 0.9805 | 1.83945 | 42.73 |
| 16 | −10.9452 | 0.1 | 1 | — |
| 17 | 4.2852 | 1.5047 | 1.51825 | 64.14 |
| 18 | −4.8107 | 1.1924 | 1.93429 | 18.9 |
| 19 | 19.3003 | 0.6302 | 1 | — |
| 20 | ∞ | 0.5 | 1.51825 | 64.14 |
| 21 | ∞ | 0.4 | 1.507 | 63.26 |
| 22 | ∞ | 0.0221 | 1 | — |
| Image pickup surface(Image plane) | ∞ | | | |

Aspheric data

1st surface k = −4.65442077E−04
A4 = 5.52805689E−03, A6 = 2.95541293E−03, A8 = −6.30538863E−05

2nd surface k = −1.98036726E−02
A4 = 7.87414302E−03, A6 = −1.01405214E−02, A8 = 1.35815047E−02

-continued

Unit mm

Various data

| Surface no. | far-point object (object distance 60 mm) | near-point object (object distance 31 mm) |
|---|---|---|
| d5 | 0.21000 | 0.83761 |
| d10 | 1.10160 | 0.47400 |

| | |
|---|---|
| far-point object distance | 60 mm |
| near-point object distance | 31 mm |
| f | 1.4595 (far-point object state) |
| f | 1.4549 (near-point object state) |
| fo | −3.018 |
| ff | 250.715 |
| ft | 2.548 |

Values of the conditional expressions are shown below.
Conditional Expression $$|(1/2) \times \beta f \times \beta t \times ((1/\beta f) - 1)| \quad (1)$$

$$Sa/FL \quad (2)$$

$$|(\beta o \times \mu f)^2 / (1 - \beta f^2)| \quad (4)$$

far-point object
near=near-point object

Example1

| | far-point object | near-point object |
|---|---|---|
| (1) | 0.028 | 0.031 |
| (2) | 0.326 | 0.330 |
| (4) | 0.008237 | — |

Example2

| | far-point object | near-point object |
|---|---|---|
| (1) | 0.040 | 0.041 |
| (2) | 0.129 | 0.130 |
| (4) | 0.007155 | — |

Example3

| | far-point object | near-point object |
|---|---|---|
| (1) | 0.00547 | 0.00610 |
| (2) | 0.430 | 0.431 |
| (4) | 0.051918 | — |

Various embodiments of the present invention have been described heretofore. However, the present invention is not restricted to these embodiments, and embodiments in which the arrangements of these embodiments are combined appropriately without departing from the scope of the present invention are also in the category of the present invention.

(Note)
An invention with the following structure is derived from these embodiments.
(Appended Mode 1)
An objective optical system consisting of, in order from an object side:
a front group;
an intermediate group; and
a rear group, wherein
a focal length varies by moving the intermediate group along an optical axis, and
in any of a far-point observation state and a near-point observation state, the objective optical system satisfies the following conditional expressions (1) and (2)

$$|(1/2) \times \beta f \times \beta t \times ((1/\beta f) - 1)| \leq 0.055 \quad (1)$$

$$0.12 \leq Sa/FL \leq 0.44 \quad (2)$$

where,
$\beta f$ denotes a lateral magnification of the intermediate group,
$\beta t$ denotes a lateral magnification of the rear group,
Sa denotes an amount of movement of the intermediate group, and
FL denotes a focal length of the objective optical system, and
conditional expressions (1) and (2) are conditional expressions for the far-point observation state (object distance 60 mm) and the near-point observation state (object distance 31 mm).
(Appended Mode 2)
The objective optical system according to appended mode 1, wherein the objective optical system includes in order from the object side, the front group having a negative refractive power, the intermediate group having a positive refractive power, and the rear group having a positive refractive power.
(Appended Mode 3)
The objective optical system according to appended mode 1, wherein the front group includes a first negative (concave) lens and a cemented lens having a negative refractive power in which a negative lens and a positive lens are cemented.
(Appended Mode 4)
The objective optical system according to appended mode 1, wherein the first negative (concave) lens has a meniscus shape having an aspheric surface.
(Appended Mode 5)
The objective optical system according to appended mode 1, wherein the intermediate group includes an aperture stop and a planoconvex lens of which an object side is a flat surface.
(Appended Mode 6)
The objective optical system according to appended mode 1, wherein the rear group includes three sets of cemented lenses.
(Appended Mode 7)
The objective optical system according to appended mode 1, wherein when a lateral magnification of the front group is let to be $\beta o$ and the lateral magnification of the intermediate group is let to be $\beta f$, the objective optical system satisfies the following conditional expression $$|(\beta o \times \beta f)^2 / (1 - \beta f^2)| > 0.006 \quad (4)$$

here, the lateral magnification is a value when the object distance is 60 mm for a far-point object and when the object distance is 31 mm for a near-point object.

(Appended Mode 8)

The objective optical system according to appended mode 1, wherein the objective optical system satisfies the following conditional expression (5)

$$0.004 \leq |(1/2) \times \beta f \times \beta t \times ((1/\beta f) - 1)| \quad (5)$$

here, the lateral magnification is a value when the object distance is 60 mm for a far-point object and when the object distance is 31 mm for a near-point object.

As described heretofore, the present invention is suitable of an objective optical system for a stereoscopic-observation endoscope having a focusing function, which enables magnified observation.

The present invention shows an effect that is possible to provide a small-size objective optical system with a reduced amount of lens drive at the time of focusing, having a safety of stereoscopic observation, in which an amount of shift in the vertical direction of a left-eye image and a right-eye image at the time of stereoscopic observation is suppressed.

What is claimed is:

1. An objective optical system consisting of, in order from an object side:
   a front group;
   an intermediate group; and
   a rear group, wherein:
   focusing is carried out from a far-point observation state to a near-point observation state by varying a focal length by moving the intermediate group along an optical axis,
   the front group includes a first negative lens, and the first negative lens has a meniscus shape having an aspheric surface,
   in the far-point observation state and the near-point observation state, the objective optical system satisfies the following conditional expressions (1) and (2)

$$|(1/2) \times \beta f \times \beta t \times ((1/\beta f))| \leq 0.055 \quad (1)$$

$$0.12 \leq Sa/FL \leq 0.44 \quad (2)$$

where,
   $\beta f$ denotes a lateral magnification of the intermediate group,
   $\beta t$ denotes a lateral magnification of the rear group,
   Sa denotes an amount of movement of the intermediate group at the time of focusing from the far-point observation state to the near-point observation state, and
   FL denotes a focal length of the objective optical system, and
   conditional expressions (1) and (2) are conditional expressions for both (i) the far-point observation state, at an object distance of 60 mm, and (ii) the near-point observation state, at an object distance of 31 mm.

2. The objective optical system according to claim 1, wherein the objective optical system comprises an objective optical system to be used in a stereoscopic endoscope.

3. The objective optical system according to claim 1, wherein the objective optical system satisfies the following conditional expression (3)

$$|(1/2) \times \beta f \times \beta t \times ((1/\beta f) - 1)| \leq 0.044 \quad (3).$$

4. An image pickup apparatus comprising the objective optical system according to claim 1.

5. An endoscope comprising the objective optical system according to claim 1.

6. An objective optical system consisting of, in order from an object side:
   a front group;
   an intermediate group; and
   a rear group, wherein:
   focusing is carried out from a far-point observation state to a near-point observation state by varying a focal length by moving the intermediate group along an optical axis,
   the intermediate group includes an aperture stop and a planoconvex lens of which an object side is a flat surface,
   in the far-point observation state and the near-point observation state, the objective optical system satisfies the following conditional expressions (1) and (2)

$$|(1/2) \times \beta f \times \beta t \times ((1/\beta f))| \leq 0.055 \quad (1)$$

$$0.12 \leq Sa/FL \leq 0.44 \quad (2)$$

where,
   $\beta f$ denotes a lateral magnification of the intermediate group,
   $\beta t$ denotes a lateral magnification of the rear group,
   Sa denotes an amount of movement of the intermediate group at the time of focusing from the far-point observation state to the near-point observation state, and
   FL denotes a focal length of the objective optical system, and
   conditional expressions (1) and (2) are conditional expressions for both (i) the far-point observation state, at an object distance of 60 mm, and (ii) the near-point observation state, at an object distance of 31 mm.

7. An image pickup apparatus comprising the objective optical system according to claim 6.

8. An endoscope comprising the objective optical system according to claim 6.

* * * * *